United States Patent [19]

Mori et al.

[11] Patent Number: 5,164,057

[45] Date of Patent: Nov. 17, 1992

[54] ELECTROPHORETIC MATRICES AND ELECTROPHORETIC METHOD USING SAME

[75] Inventors: Yuichi Mori; Masato Mikami; Hiroshi Yoshioka, all of Kanagawa, Japan

[73] Assignee: W. R. Grace & Co.-Conn., New York, N.Y.

[21] Appl. No.: 762,272

[22] Filed: Sep. 19, 1991

[51] Int. Cl.$^5$ .............................................. G01N 27/26
[52] U.S. Cl. ............................ 204/299 R; 204/182.8; 524/22
[58] Field of Search ................. 207/299 R, 182.8; 524/22

[56] References Cited

U.S. PATENT DOCUMENTS

| | | | |
|---|---|---|---|
| 4,912,032 | 3/1990 | Hoffman | 435/7 |
| 5,047,481 | 9/1991 | Siol et al. | 525/216 |
| 5,057,560 | 10/1991 | Mueller | 524/22 |
| 5,066,377 | 11/1991 | Rosenbaum et al. | 204/182.8 |

FOREIGN PATENT DOCUMENTS

| | | |
|---|---|---|
| 382214 | 8/1990 | European Pat. Off. |
| 387975 | 9/1990 | European Pat. Off. |
| 3-296657 | 12/1991 | Japan |
| WO87/06152 | 10/1987 | PCT Int'l Appl. |
| WO91/02815 | 3/1991 | PCT Int'l Appl. |

OTHER PUBLICATIONS

C. G. Meyer et al; Journal of Immunological Methods, vol. 142, No. 2, p. 251-256 (1991).

Bae et al., "Thermo-sensitive Polymers as On-Off Switches for Drug Releases," Makromol. Chem. (1987), vol. 8, pp. 481-485.

Fujushige, S., "Intrinsic Viscosity—Molecular Weight Relationships for Poly(N-isopropyl acrylamide Solutions)" Polymer Journal (1987) vol. 19, pp. 297-300.

Heskins et al., "Solution Properties of Poly(N-isopropylacrylamide)," J. Macromol. Sci.-Chem. (1968), vol. A2(8), pp. 1441-1455.

Hoffman et al., "Thermally Reversible Hydrogels: Delivery and Selective Removal of Substances from Aqueous Solutions," J. Controlled Release (1986) vol. 4, pp. 213-222.

Primary Examiner—John Niebling
Assistant Examiner—David G. Ryser
Attorney, Agent, or Firm—Beverly K. Johnson

[57] ABSTRACT

An electrophoretic matrix comprised of at least one water-insolubilized, temperature-responsive polymeric compound having an LCST is disclosed. The electrophoretic matrix can change its hydrophilic/hydrophobic property by changing temperature. A method of using the electrophoretic matrix involves charging a sample onto the matrix and carrying out electrophoresis at a temperature above or below the LCST of the polymeric compound.

9 Claims, No Drawings

ELECTROPHORETIC MATRICES AND ELECTROPHORETIC METHOD USING SAME

TECHNICAL FIELD

The present invention relates to an electrophoretic matrix comprising at least one water-insolubilized temperature-responsive polymeric compound having an LCST. More particularly, it relates to an electrophoretic matrix which can change its hydrophilic/hydrophobic property by changing temperature. The present invention also relates to an electrophoretic method of using the electrophoretic matrix.

BACKGROUND

Electrophoresis has been developed for the analysis or the separation of substances having an electrical charge, and it is the most powerful means available today particularly for the analysis of proteins. There are acidic, basic and neutral amino acids, and the proteins made of amino acids are classified into acidic, basic and neutral proteins. Proteins in a solution are electrically charged positively or negatively. When the pH of solution of a protein is changed, there is a pH at which the amounts of the positive and negative charges become entirely equal. This pH is called the isoelectric point of the protein. The proteins having an isoelectric point below pH 7 are called acidic proteins, those having an isoelectric point above pH 7 are called basic proteins, and those having an isoelectric point near pH 7 are called neutral proteins. Thus, the electrical charge of a protein is caused by the difference between the isoelectric point and the pH of the solution employed, and proteins can be separated by electrophoresis.

The conventional electrophoresis is divided into free electrophoresis and zone electrophoresis with and without a matrix, respectively. The free electrophoresis is moving boundary electrophoresis where an electric field is directly applied to a sample solution. However, this method is hardly used today because it has numerous defects such as complication of the operation, impossibility of the sample preservation, and disturbance of a pattern due to thermal convection.

The zone electrophoresis is actively used today instead of the free electrophoretic method having the above described defects. A gel-like substance such as agar gel, agarose gel, starch gel and polyacrylamide gel and a porous membrane such as cellulose acetate membrane or filter paper are used as the matrix in the zone electrophoresis and use of these matrices have solved the above described problems of the free electrophoresis.

The characteristic feature of gel electrophoresis which is one of the zone electrophoresis is the possibility of separating proteins by their molecular weights by using the molecular sieving action of the gel-like substance. Thus, when proteins are treated with sodium dodecylsulfate (hereinafter "SDS"), it is possible to unify the amounts of the electrical charges of the proteins, which is one of the two factors to control the electrophoretic mobility of proteins. The electrophoretic mobility depends on the molecular weight of proteins and thus the separation of proteins by molecular weights is possible. Isoelectric focusing which separates the proteins by converging them at their isoelectric points through creation of a pH gradient in this gel is also possible.

The characteristic feature of the porous membrane electrophoresis is its high separability by difference in electrical charge, and its practical simplicity of operation such as requirement of a very minute amount of a sample, extreme shortness of electrophoretic time, and ease of preservation of the electropherogram. Due to these reasons, the porous membrane electrophoresis is suitable for the analysis of proteins in various body fluids such as serum, urine, and spinal fluid. Thus, the gel electrophoresis is suitable for basic research work in medical and biological fields, whereas the porous membrane electrophoresis has been mainly developed as an important diagnostic method in clinical test field.

As described above, the electrical charge and the molecular weight of a protein molecule are important factors which determine the configuration of the protein in a solution. However, hydrophobic bonding is considered to be an even more important factor. Thus, the hydrophobic bonding which functions with water as its medium greatly contributes to the stabilization of proteins. It is considered that higher hydrophobicity of proteins makes the hydrophobic bonding more contribute to the protein structure.

In addition to the classification by electrical charge into acidic, basic and neutral nature as described above, the amino acids constituting proteins are also classified by the properties such as hydrophilicity and hydrophobicity. While alanine, valine, leucine, isoleucine, proline, methionine, phenylalanine and tryptophan which are electrically neutral but have a hydrophobic group in the side chain are typical hydrophobic amino acids, and glycine, serine, threonine, tyrosine, asparagine and glutamine which have a hydrophilic group in the side chain are typical hydrophilic amino acids. Therefore, it is generally considered that hydrophilicity or hydrophobicity of proteins is determined in proportion to the composition of the hydrophilic and hydrophobic amino acids.

As stated above, only the difference in molecular weights and charge density of proteins has been utilized for the separation of proteins in the conventional electrophoresis. The separation utilizing the difference in hydrophilicity and hydrophobicity of proteins, which is another important factor, has never been attempted in conventional electrophoresis. Thus, proteins having similar levels of molecular weights and charge densities but different hydrophilic/hydrophobic properties could not be separated in the past. Therefore, there exists in conventional electrophoresis a serious problem of separating highly hydrophobic lipoproteins or cell membrane associated proteins by the difference in their hydrophobic moieties or of separating highly hydrophobic sugar proteins by the difference in their hydrophilic moieties.

An object of the present invention is to provide a electrophoretic matrix which utilizes the difference in its hydrophobicity or hydrophilicity for the separation of proteins which heretofore could not be separated by prior art electrophoresis.

Another object of this invention is to provide a novel electrophoretic method which employs such an electrophoretic matrix.

SUMMARY OF THE INVENTION

The term "LCST" is used herein to mean a lower critical solution temperature which is a transition temperature of a temperature-responsive polymeric compound between hydration and dehydration.

The electrophoretic matrix in accordance with the present invention comprises at least one water-insolubilized temperature-responsive polymeric compound having a LCST.

In another aspect of the invention, an electrophretic method comprises providing a temperature gradient ranging from a temperature above the LCST of the temperature-responsive polymeric compound to a temperature below the LCST between the cathode and the anode of the electro-phoretic matrix.

DETAILED EXPLANATION OF THE INVENTION

The electrophoretic matrix of the present invention comprises at least one water-insolubilized temperature-responsive polymeric compound having an LCST.

A temperature-responsive polymeric compound shows, in the presence of water, hydrophobicity at a temperature higher than the LCST and changes to show hydrophilicity at a temperature below the LCST, and such a change is characterized by being thermally reversible.

Change of state of the temperature-responsive polymer compounds is said to be caused by hydration and dehydration. This has been explained by Haskins, M., et al in *J. Macromol. Sci. Chem.*, A2 (8), 1441, 1968, using as the sample the poly-N-isopropylacrylamide (hereinafter "PNIPAAm") which is one of such polymeric compounds. PNIPAAm is a polymeric compound which has a negative temperature coefficient of solubility. PNIPAAm shows hydrophilic property at a lower temperature because a hydrate (oxonium hydroxide), which depends on the hydrogen bond of a PNIPAAm molecule and water molecule, is formed at low temperatures. However, because the oxonium hydroxide degrades and dehydrates when temperature is raised above the LCST, the PNIPAAm molecule becomes hydrophobic and aggregates and precipitates as a result.

When a matrix comprising such a temperature-responsive polymeric compound is used as the electrophoretic matrix, electrophoresis can be performed by reversibly changing the hydrophobic or hydrophilic property of the matrix by temperature. Thus, when electrophoresis is carried out at a temperature above the LCST, hydrophobic proteins form a hydrophobic bonding with the matrix because the matrix is hydrophobic. By this reason, electrophoretic mobility of the hydrophobic proteins is reduced due to their high affinity to the matrix. On the other hand, when the temperature is lowered below the LCST, the matrix becomes hydrophilic, and accordingly the affinity to the hydrophobic proteins is decreased to release the reduction of the electrophoretic mobility. Simultaneously, the affinity between the matrix and the hydrophilic proteins increases, and this will reduce the electrophoretic mobility of hydrophilic proteins. Thus, by carrying out electrophoresis at a temperature above and below the LCST in the above described manner, proteins having similar levels of molecular weights and electrical charges can be separated by the electrophoretic method of the present invention which utilizes the difference in the hydrophilic/hydrophobic properties of the matrix.

Further, it is possible to use the matrix of the present invention which matrix comprises at least one water-insolubilized temperature-responsive polymer to perform electrophoresis by providing a temperature gradient ranging from a temperature below the LCST to a temperature above the LCST between the anode and cathode of the matrix. Thus, when the temperature of the anode side is set at a temperature below the LCST and the temperature of the cathode side is set at a temperature above the LCST, the matrix will be hydrophobic at the anode side and will become more hydrophobic toward the cathode side, and thus it is possible to provide a gradient of hydrophobicity or hydrophilicity within the matrix. Likewise, an entirely opposite gradient can be provided. In the present specification, the expression "to provide a temperature gradient between the anode and the cathode ranging from a temperature below the LCST to a temperature above the LCST" is used herein to include both temperature gradients described hereinabove. In this instance, it is preferred to continuously vary the hydrophobicity or hydrophilicity of the matrix in a wide temperature range. This can be achieved by the use of a combination of a plurality of water-insolubilized temperature-responsive polymeric compounds having different LCSTs from one another. As described above, when the matrix of the present invention having a hydrophobic or hydrophilic gradient is used for electrophoresis, even proteins having similar levels of molecular weights and electrical charges can be separated by utilizing the hydrophobic or hydrophilic gradient.

Furthermore, it is possible to separate a sample more accurately and clearly by changing the temperature above or below the LCST after charging the sample to be separated in the electrophoretic matrix of the present invention. For example, a sample is contacted with the matrix of the present invention at a temperature below the LCST and electrophoresis can be carried out at a temperature above the LCST, or the sample is contacted with the matrix at a temperature above the LCST and electrophoresis can be carried out at a temperature below the LCST. The electrophoresis method of the present invention includes the electrophoretic method which comprises the operations represented by the above described embodiments.

The above described change can be similarly observed in the system where crosslinks have been incorporated in the temperature-responsive polymeric compound and also in the system where the polymeric compound has been graft-polymerized.

The temperature-responsive polymeric compounds which are insolubilized in water before use for the electrophoretic matrix of the present invention includes, for examples, poly-N-substituted acrylamide or methacrylamide derivatives and their copolymers, polyvinylmethyl ether, polyethylene oxide, etherized methylcellulose, and partially acetylated polyvinyl alcohol. Particularly preferred are poly-N-substituted methacrylamide or acrylamide derivatives and their copolymers, polyvinylmethyl ether, and partially acetylated polyvinyl alcohol.

Preferred examples of such temperature-responsive polymeric compounds are listed below. The LCSTs of these polymers rise with the sequence of polymers listed below.

Poly-N-acryloyl piperidine
Poly-N-n-propyl methacrylamide
Poly-N-isopropyl acrylamide
Poly-N,N-diethyl acrylamide
Poly-N-isopropyl methacrylamide
Poly-N-cyclopropyl acrylamide
Poly-N-acryloyl pyrrolidine
Poly-N,N-ethylmethyl acrylamide
Poly-N-cyclopropyl methacrylamide Poly-N-ethyl acrylamide The above described polymers may be homopolymers or copolymers with other monomers. Any hydrophilic monomers and hydrophobic monomers can be used as the monomers for copolymerization. Generally speaking, copolymerization with a hydrophilic monomer will raise the LCST, and copolymerization with a hydrophobic monomer will lower the LCST. With a proper selection of monomers, a copolymer with a desired LCST can be achieved.

Example of suitable hydrophilic monomers are N-vinylpyrrolidine, vinylpyridine, acrylamide, methacrylamide, N-methyl acrylamide, hydroxyethyl methacrylate, hydroxyethyl acrylate, hydroxymethyl methacrylate, hydroxymethyl acrylate, acrylic acid, methacrylic acid and their salts, vinylsulfonic acid and styrylsulfonic acid and N,N-dimethylaminoethyl methacrylate, N,N-diethylaminoethyl methacrylate, N,N-dimethylaminopropyl acrylamide and their salts, but the present invention is not limited to these compounds.

Examples of suitable hydrophobic monomers are acrylate or methacrylate derivatives such as ethyl acrylate, methyl methacrylate, n-butyl acrylate, n-butyl methacrylate, glycidyl methacrylate; N-substituted alkyl acrylamide or methacrylamide derivatives such as N-n-butyl acrylamide or methacrylamide; vinyl chloride; acrylonitrile; styrene; and vinyl acetate but the present invention is not limited to these compounds.

One of the method of insolubilizing the above described temperature-responsive polymeric compounds in water is to incorporate crosslinks in these polymeric compounds.

For example, when the electrophoretic matrix is prepared from the above described temperature responsive polymeric compound alone, a membrane casting method is preferably employed. The pore size and the porosity of the membrane can be regulated by the membrane casting conditions such as the solvent selected, the concentration of the polymeric compound chosen, the temperature employed and the coagulant selected. The pore size which can be employed for the electrophoretic matrix of the present invention is typically 0.1 to 100 $\mu$m, preferably 0.1 to 5 $\mu$m, and the porocity is typically 10% to 95% and preferably 50% to 90%.

The membrane of the polymeric compound thus obtained is irradiated with light, electron rays and gamma rays to incorporate intermolecular crosslinks in these polymeric compounds.

Another method of insolubilizing the temperature-responsive polymeric compounds in water is to copolymerize at least one monomer used for forming the temperature-responsive polymeric compounds described hereinabove and a bifunctional monomer copolymerizable therewith, such as N,N-methylenebisacrylamide, hydroxethyl dimethacrylate and divinylbenzene to give a copolymer having a crosslinked structure by conventional methodology.

Still another method of insolubilizing the temperature-responsive polymeric compounds in water is to coat the polymeric compounds in an aqueous solution on the surface of a supporting material and to irradiate the polymeric compounds with light, electron rays or gamma rays to incorporate intermolecular crosslinks in these polymeric compounds.

A further method of insolubilizing the temperature-responsive polymeric compounds in water is to graft-polymerize at least one monomer used for forming the temperature-responsive polymeric compounds on the surface of a supporting material by selecting an appropriate conventional method depending upon such properties as the material of the supporting material and its shape. For example, graft polymerization can be carried out onto the surface of the supporting material in the form of a plate, a film or a flat membrane by low temperature plasma polymerization without losing the properties of the supporting material as such. In addition, conventional graft polymerization techniques such as the ozone oxidation process and the cerium ion treatment process can be employed in the present invention.

Still another method of insolubilizing the temperature-responsive polymeric compounds in water is to graft-polymerize the temperature-responsive polymeric compound on the surface of a supporting material.

The supporting materials which can be employed in the present invention include, for example, porous substances such as porous acetyl cellulose membranes, porous polyethylene membranes, porous polypropylene membranes and porous polytetrafluoroethylene membranes, porous polydimethylsiloxane membranes, porous polyester membranes, porous polycarbonate membranes and porous polymethyl methacrylate membranes.

When the porous supporting materials are employed, it is preferred that a desired pore size, a desired porosity and a desired shape are previously selected. Also it is preferred that the number average molecular weight of the temperature-responsive polymeric compound is not greater than 5,000, most preferably from about 500 to 5,000, in order to avoid covering the pores. Such temperature-responsive polymeric compounds having a number average molecular weight of not greater than 5,000 can be incorporated into the supporting material by, first, introducing a reactive functional group at the terminal of the polymeric compound having a number average molecular weight of not greater than 5,000 by the chain transfer reaction and, second, allowing the reactive functional group thus introduced to react with the previously introduced functional group on the surface of the supporting material capable of reacting with the reactive functional group.

The present invention is further explained by the following examples which are given for illustrative purposes and are not meant to limit the invention.

EXAMPLE 1

Commercially available cellulose acetate membrane ("Separax S", pore size: about 2 $\mu$m, porosity: 80%, size: 2$\times$22 cm, a product of Fuji Film K.K.) was placed in a tube, and N-isopropyl acrylamide (hereinafter "NIPAAm") 5 g and water 30 ml were injected. Then, 10 ml of a 0.1N aqueous nitric acid solution containing cerium ammonium nitrate 2 mg was added dropwise, and graft reaction was carried out at 20° C. for one hour in a nitrogen atmosphere. After the reaction, the reaction mixture was washed with water, and dried in vacuum. The graft polymerization ratio of the porous membrane grafted with poly-N-isopropyl acrylamide (hereinafter "CA-graft-PNIPAAm") was calculated from the dry weight before the reaction and the dry weight after the reaction, and it was about 5%.

A mixture of bovine serum albumin and ovoalbumin was analyzed by an ordinary cellulose acetate membrane electrophoretic apparatus by using the CA-graft-PNIPAAm membrane thus obtained. A phosphate buffered saline (PBS) solution of equal amounts of bovine serum albumin and ovoalbumin having a concentration of about 10 g/dl was prepared as the sample to be separated. As a control, an about 0.5 μl solution of the protein mixture was coated on the commercially available cellulose acetate membrane as described above, and a constant current of 0.8 mA was applied for about 45 minutes at 37° C. Then the cellulose acetate film was made transparent with decalin and the proteins were analyzed by densitometry. There was only one peak, and thus bovine serum albumin and ovoalbumin were not separated.

On the other hand, the CA-graft-PNIPAAm membrane as obtained above in accordance with the present invention was allowed to be hydrophilically by being left to stand at about 20° C. for about 15 minutes. After coating the same protein mixture as above on the CA-graft-PNIPAAm membrane electrophoresis was carried out at 37° C. under the same conditions as above. As a result, two peaks corresponding to bovine serum albumin and ovoalbumin, respectively, were observed. That is, the mobility of bovine serum albumin was faster than that of ovoalbumin.

Furthermore, electrophoresis was carried out in the same manner as described above by using the CA-graft-PNIPAAm membrane while keeping the anode side at about 37° C. and the cathode side at about 20° C. As a result, two peaks of bovine serum albumin and ovoalbumin were more clearly observed at different positions.

This indicates that it is now possible to separate bovine serum albumin and ovoalbumin having different hydrophobicities, by using the CA-graft-PNIPAAm membrane of the present invention.

What is claimed is:

1. An electrophoretic matrix comprising at least one water-insolubilized temperature-responsive polymeric compound having an LCST.

2. The matric of claim 1, wherein said polymeric compound is selected from the group consisting of a poly-N-substituted acrylamide derivative, a poly-N-substituted methacrylamide derivative, their copolymers, polyvinylmethyl ether and partially acetylated polyvinyl alcohol.

3. The matrix of claim 1, wherein said polymeric compound is provided on a supporting material.

4. The matrix of claim 3, wherein said polymeric compound is grafted on the surface of said supporting material.

5. The matrix of claim 3, wherein said supporting material is a porous membrane.

6. The matrix of claim 5, wherein said porous membrane is selected from the group consisting of a porous acetyl cellulose membrane, a porous polyethylene membrane, a porous polypropylene membrane and a porous polytetrafluoroethylene membrane, a porous polydimethylsiloxane membrane, a porous polyester membrane, a porous polycarbonate membrane and a porous polymethyl methacrylate membrane.

7. The matrix of claim 6, wherein the number average molecular weight of said temperature-responsive polymeric compound is not greater than 5,000.

8. The matrix of claim 3, wherein said temperature-responsive polymeric compound is a combination of a plurality of water-insolubilized temperature-responsive polymeric compounds having different LCSTs from one another.

9. The matrix of claim 1, wherein said temperature-responsive polymeric compound is a combination of a plurality of water-insolubilized temperature-responsive polymeric compounds having different LCSTs from one another.

* * * * *

UNITED STATES PATENT AND TRADEMARK OFFICE
CERTIFICATE OF CORRECTION

PATENT NO. : 5,164,057
DATED : November 17, 1992
INVENTOR(S) : Yuichi Mori, Masato Mikami & Hiroshi Yoshioka It is certified that error appears in the above-indentified patent and that said Letters Patent is hereby corrected as shown below:

Column 8, claim 2, line 1, change "matric" to --matrix--

Signed and Sealed this

Eighteenth Day of January, 1994

*Attest:*

BRUCE LEHMAN

*Attesting Officer*   *Commissioner of Patents and Trademarks*